(12) United States Patent
Mestl et al.

(10) Patent No.: US 8,722,565 B2
(45) Date of Patent: May 13, 2014

(54) METHOD FOR APPLYING A WASH COAT SUSPENSION TO A CARRIER STRUCTURE

(75) Inventors: Gerhard Mestl, München (DE);
Christian Gückel, Grafing (DE);
Marvin Estenfelder, Arona (IT);
Bastian Käding, Novara (IT)

(73) Assignee: Sued-Chemie IP GmbH & Co. KG, Munich (DE)

( * ) Notice: Subject to any disclaimer, the term of this patent is extended or adjusted under 35 U.S.C. 154(b) by 269 days.

(21) Appl. No.: 12/601,876

(22) PCT Filed: Jun. 2, 2008

(86) PCT No.: PCT/EP2008/004398
§ 371 (c)(1),
(2), (4) Date: May 25, 2010

(87) PCT Pub. No.: WO2008/145405
PCT Pub. Date: Dec. 4, 2008

(65) Prior Publication Data
US 2010/0311573 A1    Dec. 9, 2010

(30) Foreign Application Priority Data
May 31, 2007    (DE) .......................... 10 2007 025 357

(51) Int. Cl.
*B01J 8/18* (2006.01)
*B65G 53/40* (2006.01)

(52) U.S. Cl.
USPC ........... 502/170; 422/143; 422/144; 422/145; 406/117

(58) Field of Classification Search
None
See application file for complete search history.

(56) References Cited

U.S. PATENT DOCUMENTS

| 4,259,211 A | 3/1981 | Krabetz et al. |
| 4,970,804 A | 11/1990 | Huettlin |
| 5,145,650 A * | 9/1992 | Huttlin .......................... 422/143 |
| 6,367,165 B1 | 4/2002 | Huettlin |

(Continued)

FOREIGN PATENT DOCUMENTS

| DE | 199 04 147 A1 | 8/2000 |
| DE | 102 48 116 B3 | 4/2004 |

(Continued)

OTHER PUBLICATIONS

International Search Report, Oct. 21, 2008.

*Primary Examiner* — Melvin C Mayes
*Assistant Examiner* — Colette Nguyen
(74) *Attorney, Agent, or Firm* — RatnerPrestia

(57) ABSTRACT

A method for applying a washcoat suspension to a support structure. To provide coatings with largely uniform thickness starting from washcoat suspensions, the method uses a device (10) set up to produce, by means of a process gas (40), a fluid bed of support structures in which the support structures circulate elliptically or toroidally, the method comprising the steps of:

Figure 1A:
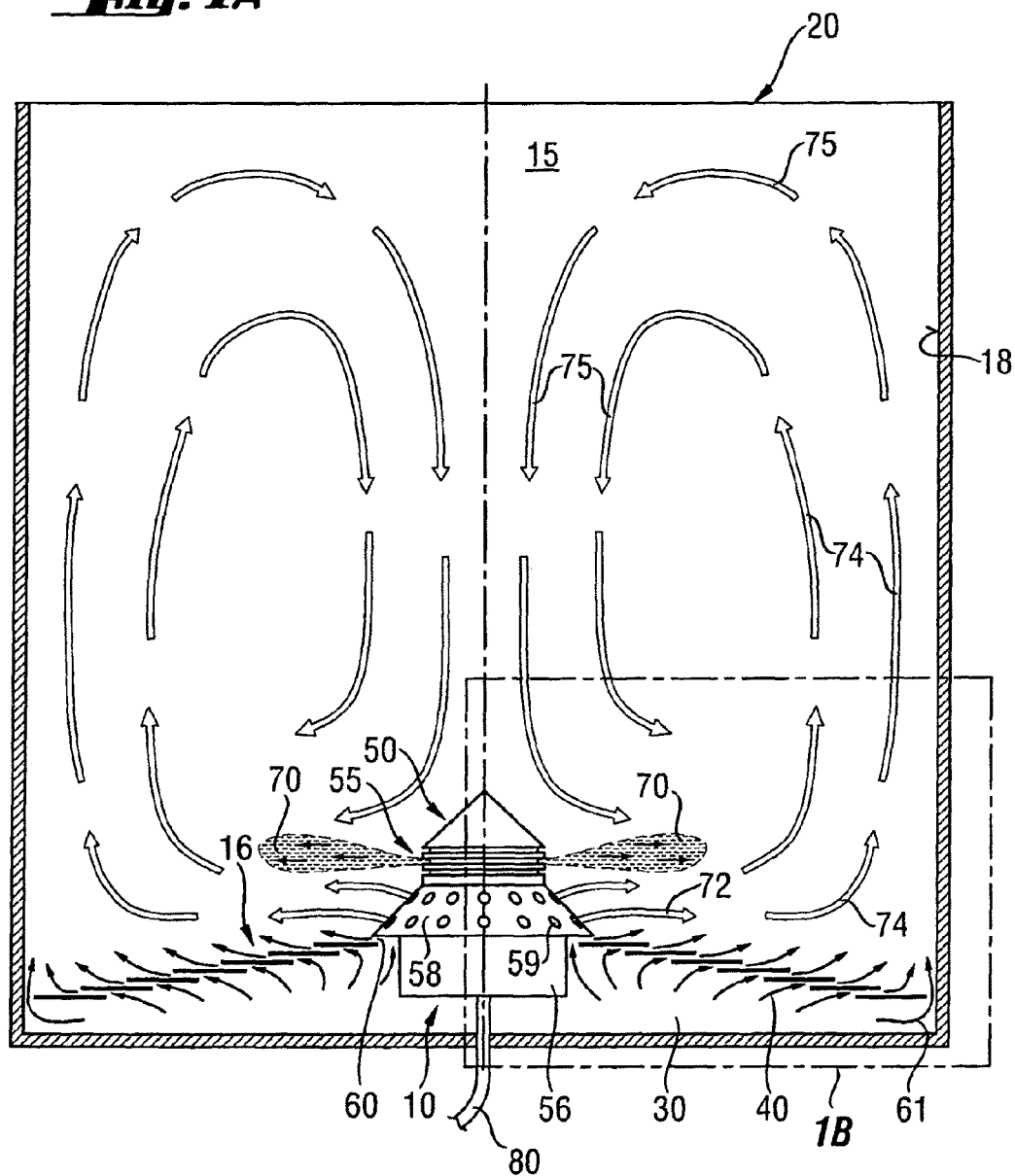

a) charging the device (10) with support structures and producing a support-structure fluid bed by means of a process gas (40), wherein the support structures circulate in the fluid bed elliptically or toroidally, preferably toroidally;

b) impregnating the support structures with a washcoat suspension by spraying the support structures circulating elliptically or toroidally in the fluid bed with the washcoat suspension;

c) drying the support structures sprayed with the washcoat suspension; and d) optionally calcining the support structures loaded with the solids contents of the washcoat suspension.

32 Claims, 6 Drawing Sheets

(56) References Cited

U.S. PATENT DOCUMENTS

| | | |
|---|---|---|
| 6,949,141 B2 | 9/2005 | Huettlin |
| 2007/0041795 A1* | 2/2007 | Neto et al. .................... 406/117 |
| 2007/0234586 A1 | 10/2007 | Huettlin |
| 2009/0105507 A1* | 4/2009 | Dubois et al. ................. 568/594 |

FOREIGN PATENT DOCUMENTS

| | | | |
|---|---|---|---|
| DE | WO 2005/030380 | * | 5/2005 |
| DE | WO2006/027009 | * | 3/2006 |
| DE | 20 2005 003 791 U1 | | 7/2006 |
| DE | 10 2005 055 827 A1 | | 5/2007 |
| EP | 0 370 167 A1 | | 5/1990 |
| EP | 0 436 787 B1 | | 7/1991 |
| JP | 2006-255600 | | 9/2006 |
| JP | 2007-506540 | | 3/2007 |
| WO | WO 2005 030380 A | | 4/2005 |
| WO | WO 2006 027009 A | | 3/2006 |

* cited by examiner

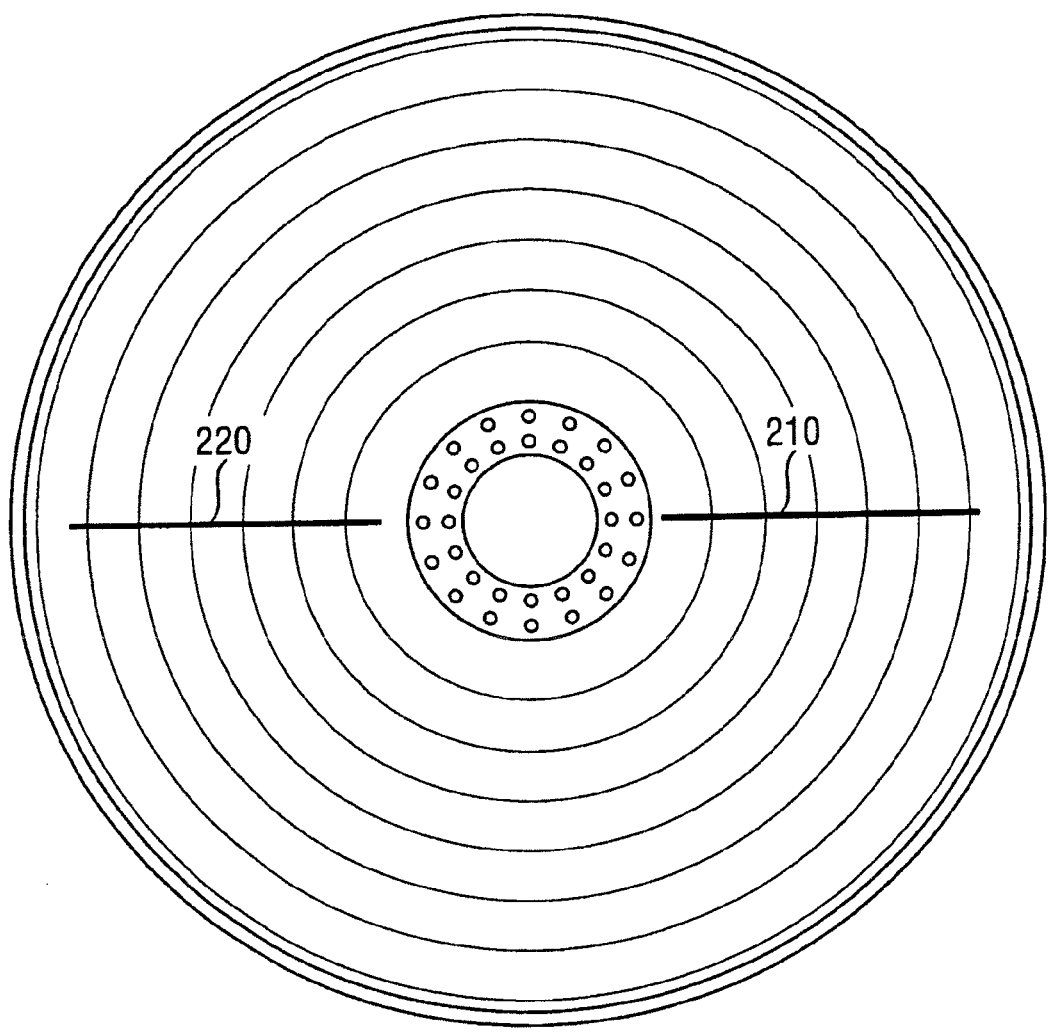

METHOD FOR APPLYING A WASH COAT SUSPENSION TO A CARRIER STRUCTURE

CROSS-REFERENCE TO RELATED APPLICATION

This is a National Phase application of PCT application number PCT/EP2008/004398, filed Jun. 2, 2008, which claims priority benefit of German application number DE 10 2007 025 357.7, filed May 31, 2007, the content of such applications being incorporated herein by reference.

FIELD OF THE INVENTION

The present invention relates to a method for applying a washcoat suspension to a support structure.

BACKGROUND OF THE INVENTION

Shell catalysts and methods for their production are known in the state of the art. Particular shell catalysts are produced for example by applying a washcoat suspension containing a powdery support oxide and a catalytically active species to a support structure in the form of a shell. With shell catalysts, a more selective reaction control is possible in many cases than with catalysts which are loaded with the catalytically active species into the core of the support structure.

Phthalic anhydride (PA) for example is currently produced predominantly by means of shell catalysts in high selectivity. The great majority of the shell catalysts currently used for producing PA are shell catalysts with a shell comprising $V_2O_5/TiO_2$ on a non-porous steatite support formed as a hollow cylinder. The active-metal oxide $V_2O_5$ is probably not present in the $V_2O_5/TiO_2$ system of these catalysts only in the form of crystalline $V_2O_5$ particles. Such shell catalysts are usually produced by coating using appropriate suspensions in coating drums or fluid-bed units.

However, the above-named techniques have reached their limits as regards the homogeneity of the layer thickness of correspondingly produced shell catalysts, in fact as regards both the homogeneity of the layer thickness of an individual shell catalyst and that of a batch of shell catalysts.

DESCRIPTION OF THE INVENTION

It is therefore the object of the present invention to provide a method by means of which coatings with largely uniform thickness starting from washcoat suspensions can be applied to a support structure.

This object is achieved by a method using a device which is set up to produce, by means of a process gas, a fluid bed of support structures in which the support structures circulate elliptically or toroidally, preferably toroidally, said method comprising the steps of
 a) charging the device with support structures and producing a support-structure fluid bed by means of a process gas, wherein the support structures circulate in the fluid bed elliptically or toroidally, preferably toroidally;
 b) impregnating the support structures with a washcoat suspension by spraying the support structures circulating elliptically or toroidally in the fluid bed with the washcoat suspension;
 c) drying the support structures sprayed with the washcoat suspension;
 d) optionally calcining the support structures loaded with the solids contents of the washcoat suspension.

Surprisingly, it has been established that support structures with a largely uniform layer thickness can be coated by means of the method according to the invention.

Washcoat suspensions are known in the state of the art. These are suspensions which contain at least one metal oxide (e.g. $Al_2O_3$, $TiO_2$, $ZrO_2$, etc.) in particulate form. Mixtures of different metal oxides can also be used. The metal oxides are normally dispersed in a suspending agent, in most cases water, and then applied to a support. The application most often takes place by dipping or spraying methods. In addition, still further loading materials, such as binders, fillers, stabilizers, promoters or the like, can be contained in the suspension. During and/or after the application of the washcoat suspension, this is dried and optionally calcined. Depending on the use in the process of the coating catalyst, the washcoat can be impregnated in the following steps for example with, or with further, catalytically active material, for example by dipping, spraying, impregnating and the like, wherein normally further drying and optionally calcining and/or reducing steps can subsequently take place.

In the method according to the invention, a fluid bed is produced in which the support structures circulate elliptically or toroidally. In the state of the art, the transition of the particles of a bed into a state in which the particles can move completely freely (fluid bed) is called the loosening point (incipient fluidization point) and the corresponding fluidization velocity is called the loosening velocity. According to the invention it is preferred that in the method according to the invention the fluidization velocity is up to 4 times the loosening velocity, preferably up to three times the loosening velocity and more preferably up to 2 times the loosening velocity.

According to an alternative embodiment of the method according to the invention, it can be provided that the fluidization velocity is up to 1.4 times the common logarithm of the loosening velocity, preferably up to 1.3 times the common logarithm of the loosening velocity and more preferably up to 1.2 times the common logarithm of the loosening velocity.

Within the framework of the method according to the invention, the support structures sprayed with the suspension are preferably dried continuously by means of the process gas. However, it can also be provided that a separate final drying step is carried out after impregnation accompanied by continuous drying. In the first case, for example, the drying speed and thus for example the uniformity of the thickness of the shell can be set by the temperature of the process gas or of the support structures, in the second case the drying can be carried out using any drying method known to a person skilled in the art to be suitable.

Devices for carrying out the method according to the invention are described for example in WO 2006/027009 A1, DE 102 48 116 B3, EP 0 370 167 A1, EP 0 436 787 B1, DE 199 04 147 A1, DE 20 2005 003 791 U1, the contents of which are incorporated in the present invention through reference.

Further suitable fluid-bed units preferred according to the invention are sold for example by Glatt GmbH (Binzen, Germany), Aeromatic-Fielder AG (Bubendorf, Switzerland), Fluid Air Inc. (Aurora, Ill., USA), Oystar Huttlin GmbH (Schopfheim, Germany), Umang Pharmatech Pvt. Ltd. (Marharashtra, India) and Innojet Technologies (Steinen, Germany).

Fluid-bed devices which are particularly preferred for carrying out the method according to the invention are sold by Innojet Technologies under the names Innojet® Ventilus or Innojet® AirCoater. These devices comprise a cylindrical container with a fixedly and immovably installed container bottom in the centre of which a spraying nozzle is mounted.

The bottom consists of annular plates arranged in steps above each other. The process air flows horizontally into the container between the individual plates eccentrically, with a circumferential flow component, outwardly towards the container wall. So-called air-flow beds form on which the support structures are first transported outwardly towards the container wall. A perpendicularly oriented process air stream which deflects the support structures upwards is guided outside along the container wall. Having reached the top, the support structures move on a more or less tangential path back towards the centre of the bottom, in the course of which they pass through the spray mist of the nozzle. After passing through the spray mist, the described movement process begins again. The described process-air guiding provides the basis for a largely homogeneous, toroidal fluid-bed-like circulating movement of the support structures.

Unlike a corresponding conventional fluid bed, the effect of the combined action of the spraying and the fluid-bed-like elliptical or torus-like circulating movement of the support structures in the fluid bed is that the individual support structures pass through the spray nozzle at an approximately identical frequency. In addition, the circulation process also sees to it that the individual support structures rotate about their own axis, for which reason the support structures are coated particularly evenly.

In the method according to the invention the support structures circulate in the fluid bed elliptically or toroidally, preferably toroidally. To give an idea of how the structures move in the fluid bed, it may be stated that in the case of "elliptical circulation" the support structures move in the fluid bed in a vertical plane on an elliptical path, the size of the major and minor axes changing. In the case of "toroidal circulation" the support structures move in the fluid bed in the vertical plane on an elliptical path, the size of the major and minor axes changing, and in the horizontal plane on a circular path, the size of the radius changing. On average, the support structures move in the case of "elliptical circulation" in the vertical plane on an elliptical path, in the case of "toroidal circulation" on a toroidal path, i.e. a support structure covers the surface of a torus helically with a vertically elliptical section.

According to a preferred embodiment of the method according to the invention, it is provided that the device comprises a process chamber—for receiving support structures—with a bottom in the centre of which an annular gap nozzle is arranged.

To produce a support-structure fluid bed in which the support structures circulate elliptically or toroidally in a manner that is simple in terms of process engineering and thus inexpensive, it is provided according to a further preferred embodiment of the method according to the invention that the process chamber comprises a side wall, wherein the process gas is fed, with a horizontal movement component aligned radially outwards, into the process chamber through the bottom of the process chamber, the bottom being preferably constructed of several overlapping annular guide plates laid one over the other between which annular slots are formed.

Because process gas is fed into the process chamber with a horizontal movement component aligned radially outwards, an elliptical circulation of the support structures in the fluid bed is brought about. If the structures are to circulate toroidally in the fluid bed, the support structures must also be subjected to a further circumferential movement component which forces the structures onto a circular path. The structures can be subjected to this circumferential movement component for example by attaching suitably oriented guide rails to the side wall in order to deflect the support structures. According to a further preferred embodiment of the method according to the invention, however, it is provided that the process gas fed into the process chamber is subjected to a circumferential flow component. The production of the fluid bed in which the supports circulate toroidally is thereby ensured in a simple manner in terms of process engineering.

To subject the process gas fed into the process chamber to the circumferential flow component, it can be provided according to a preferred embodiment of the process according to the invention that suitably shaped and oriented process gas guide elements are arranged between the annular guide plates. As an alternative or in addition to this, it can be provided that the process gas fed into the process chamber is subjected to the circumferential flow component by feeding additional process gas, with a movement component aligned diagonally upwards, through the bottom of the process chamber into the process chamber, preferably in the area of the side wall of the process chamber.

It can be provided that the structures circulating in the fluid bed are sprayed with the suspension by means of the annular gap nozzle by having this spray a spray cloud, wherein the plane of symmetry of the spray cloud runs parallel to the plane of the device bottom or the spray cloud is oriented diagonally upwards. Due to the 360° circumference of the spray cloud, the support structures moving centrally downwards can be sprayed particularly evenly with the solution. The annular gap nozzle, i.e. its mouth, is preferably completely embedded in the fluid bed. The process air of the toroidal fluid bed is supported by the preferably diagonally upwardly oriented spraying direction.

As already stated above, it is provided according to a further preferred embodiment of the method according to the invention that the annular gap nozzle is centrally arranged in the bottom of the container and the mouth of the annular gap nozzle is completely embedded in the fluid bed. It is thereby ensured that the distance covered by the drops of the spray cloud until they meet a support is relatively short and, accordingly, relatively little time remains for the drops to coalesce into larger drops, which could work against the formation of a largely uniform shell thickness.

According to a further preferred embodiment of the method according to the invention, it can be provided that a gas support cushion is produced on the underside of the spray cloud. The bottom cushion keeps the bottom surface largely free of sprayed suspension, which means that almost all of the sprayed suspension is introduced into the fluid bed, with the result that hardly any spray losses occur.

According to a further preferred embodiment of the method according to the invention, it can be provided that the support structure is formed from a non-porous (compact) material or material mixture, preferably from steatite, quartz ($SiO_2$), porcelain, magnesium oxide, tin dioxide, silicon carbide, rutile, alumina ($Al_2O_2$), aluminium silicate, magnesium silicate, zirconium silicate or from cerium silicate or from mixtures of two or more of the above materials.

During the circulation of the support structures within the framework of the method according to the invention, these are subjected to a mechanical load stress, which can result in a degree of wear of the already coated-on washcoat. In particular in order to keep the wear of the structures within reasonable limits, the support structure has a hardness greater than/equal to 20 N, preferably greater than/equal to 30 N, further preferably greater than/equal to 40 N, most preferably greater than/equal to 80 N and in particular 20 to 150 N. The hardness is ascertained by means of an 8M tablet-hardness testing machine from Dr. Schleuniger Pharmatron AG, determining the average for 99 structures after drying at 130° C. for 2 h, wherein the apparatus settings are as follows:

| | |
|---|---|
| Hardness: | N |
| Distance from the shaped body: | 5.00 mm |
| Time delay: | 0.80 s |
| Feed type: | 6 D |
| Speed: | 0.60 mm/s |

On the grounds of cost, air is preferably used as process gas in the method according to the invention. It can also be provided that an inert gas is used as process gas, for example nitrogen, methane, short-chain saturated hydrocarbons, one of the noble gases, preferably helium, neon or argon, a halogenated hydrocarbon or mixtures thereof.

According to a further preferred embodiment of the method according to the invention, the process gas can be recycled into the device in a closed loop, above all in the case of expensive gases such as e.g. helium, argon, etc.

According to a further preferred embodiment of the method according to the invention, the support structures are heated prior to and/or during the application of the suspension, for example by means of a heated process gas. According to a further preferred embodiment of the method according to the invention, the process gas is heated, preferably to a temperature of more than/equal to 40° C., by preference to a temperature of more than/equal to 60° C., further preferably to a temperature of more than/equal to 70° C. and most preferably to a temperature of 60 to 100° C.

To prevent drops of the spray cloud from drying prematurely, it can be provided according to a further preferred embodiment of the method according to the invention that the process gas is enriched, before being fed into the device, with the suspending agent of the suspension, preferably in a range of to 50% of the saturation vapour pressure (at process temperature).

According to a further preferred embodiment of the method according to the invention, the suspending agent added to the process gas and also suspending agents from the drying of the structures can be separated from the process gas by means of suitable cooling aggregates, condensers and separators and returned to the suspending agent enricher by means of a pump.

It is preferred that the support structure is formed as a sphere, cylinder, perforated cylinder, trilobe, tetralobe, ring, doughnut, star, cartwheel or as a strand, preferably as a ribbed strand or star strand.

Furthermore, it is preferred that the washcoat suspension contains $TiO_2$, $V_2O_5$ and $Sb_2O_3$ in particulate form. In addition or as an alternative to this, metal oxides, such as e.g. $SiO_2$, $Al_2O_3$, $ZrO_2$, zeolites, $Cr_2O_3$, $MoO_3$, $WO_3$, $Nb_2O_5$, $Ta_2O_5$, $Fe_2O_3$ can also be contained in the suspension.

It is further preferred that the suspension furthermore comprises a phosphate compound, an alkali or alkaline earth compound, e.g. caesium compound, and an organic and/or inorganic binding agent.

It is also preferred that the washcoat suspension is sprayed onto a ring as support structure.

In addition, it is preferred that the washcoat suspension contains iron molybdate.

Furthermore, it is preferred that the washcoat suspension contains a mixed oxide of Mo, V and W, or Mo, V and Nb, or Ta and optionally Te or Sb, which is preferably doped with Cu, Mn or Fe.

The present invention furthermore relates to a shell catalyst produced according to the method according to the invention, comprising as support structure a shaped body to which a shell comprising a metal-oxide material is applied, wherein the shell catalyst is an element of a batch of a plurality of shell catalysts, wherein the ratio of the standard deviation of the shell thicknesses of the shell catalysts of the batch to the mean value of the shell thicknesses of the shell catalysts of the batch is smaller than/equal to 20%, preferably smaller than/equal to 15%, by preference smaller than/equal to 12% and more preferably smaller than/equal to 10% or 3 to 18%, preferably 3 to 15%. Such shell catalysts can be obtained by means of the method according to the invention.

The shell thickness of an individual shell catalyst is preferably determined as an mean value by cutting the shell catalyst in half and determining the layer thicknesses under the microscope at 4 points at 90° intervals.

The standard deviation is determined according to the formula $$\sigma_x = \sqrt{\frac{1}{N-1}\sum_{i=1}^{N}(X_i - \overline{X})^2}$$

in which
$\sigma_x$ is the standard deviation;
N (=100) is the size of the random sample (number of support structures; N is equal to 100);
$X_i$ is the shell thickness on the i-th support of the random sample;
$\overline{X}$ is the empirical mean value of the shell thickness of the random sample (thus the arithmetic mean of the random sample), which is determined according to the formula $$\overline{X} = \frac{1}{N}\sum_{i=1}^{N} X_i$$

Such shell catalyst batches can be produced by means of the method according to the invention.

The present invention furthermore relates to the use of a device which is set up to produce, by means of a process gas, a fluid bed of support structures in which the structures circulate elliptically or toroidally, preferably toroidally, for applying a washcoat suspension to a support structure or for carrying out the method according to the invention.

According to a preferred embodiment of the use according to the invention, it is provided that the device comprises a process chamber with a bottom in the centre of which an annular gap nozzle is arranged.

According to a preferred embodiment of the use according to the invention, it is provided that the process chamber comprises a side wall and a bottom, wherein the bottom is constructed of several overlapping annular guide plates laid one over another between which annular slots are formed via which process gas can be fed in with a horizontal movement component aligned radially outwards. The formation of a fluid bed in which the shaped bodies circulate elliptically or toroidally in a particularly uniform manner is thereby made possible in a manner that is simple in terms of process engineering, which is accompanied by an increase in product quality.

In order to ensure a particularly uniform spraying of the structures, it can be provided according to a further embodiment that the mouth of the nozzle is formed such that a spray cloud, the horizontal mirror plane of which runs parallel to the bottom plane, can be sprayed with it.

According to a further preferred embodiment of the use according to the invention, it is provided that a spray cloud which is oriented diagonally upwards can be sprayed with the nozzle, preferably a spray cloud in the form of a spray cone oriented upwards, wherein this preferably supports the process air.

It can furthermore be preferred that outlets for support gas are provided between the mouth of the annular gap nozzle and the bottom lying beneath it, in order to produce a support cushion on the underside of the spray cloud. The bottom air cushion keeps the bottom surface free of sprayed suspension.

According to a further preferred embodiment of the use according to the invention, the support gas in the device is provided by the annular gap nozzle itself and/or by process gas. These measures allow the support gas to be produced in a wide variety of ways. At the annular gap nozzle itself outlets can be provided via which some of the spray gas emerges in order to contribute to the formation of the support gas. In addition or alternatively, some of the process gas which flows through the bottom can be guided towards the underside of the spray cloud and thereby contribute to the formation of the support gas.

According to a further embodiment of the invention, the annular gap nozzle has a conical or hyperbolic head and the mouth runs along a circular conical section surface. It is thereby ensured that the structures moving vertically downwards are led uniformly and in a targeted manner through the cone to the spray cloud which is sprayed from the circular spray gap in the lower end of the cone.

According to a further embodiment of the use, there is provided in the area between mouth and bottom lying beneath it a truncated-cone-shaped or hyperbolic wall which preferably has passage openings for support gas. This measure has the advantage that the previously mentioned harmonic deflection movement at the cone is maintained by the continuation over the truncated cone and in this area support gas can emerge through the passage openings and provide the corresponding support on the underside of the spray cloud.

In a further version of the use according to the invention, an annular slot for the passage of process gas is formed between the underside of the truncated-cone-shaped or hyperbolic wall. This measure has the advantage that the transfer of the support structures onto the air cushion of the bottom can be particularly well controlled and can be carried out in a targeted manner beginning in the area immediately underneath the nozzle.

In order to be able to introduce the spray cloud into the fluid bed at the desired height, it is preferred that the position of the mouth of the nozzle is height-adjustable.

According to a further version of the use according to the invention, guide elements which impose a circumferential flow component on the process gas passing through are arranged between the annular guide plates.

The following examples serve to illustrate the invention.

Comparison Example 1

Phthalic Anhydride (PA) Catalyst

To produce a catalyst with an active-mass content of 8 wt.-% and composed of 7.5 wt.-% vanadium pentoxide, 3.2 wt.-% antimony trioxide, 0.40 wt.-% caesium (calculated as caesium), 0.2 wt.-% phosphorus (calculated as phosphorus), the remainder being titanium dioxide, in a so-called fluid-bed coater (Unilab®, Oystar Huttlin, Schopfheim, Germany), 2600 g of steatite bodies in the form of hollow cylinders measuring 8×6×5 mm were coated with a suspension of 17.9 g of vanadium pentoxide, 7.6 g of antimony trioxide, 1.28 g of caesium sulphate, 1.9 g of ammonium dihydrogenphosphate, 364.4 g of titanium dioxide with a BET surface area of 26 $m^2/g$, 130.5 g of binding agent comprising a 50% dispersion of water and vinyl acetate/ethylene copolymer (EP 65, Air Products) and 1000 g of water. For this, the suspension was sprayed onto a fluid bed produced by means of process air temperature-controlled at 80° C.

50 hollow cylinders were removed, cut in half and the layer thicknesses determined under the microscope at 4 points at 90° intervals. The layer thickness of a hollow cylinder corresponds to the mean value of the 4 measured values. 72% of all the shaped bodies measured had a layer thickness of 158 μm.

Example 1

Catalysts were produced analogously to comparison example 1, differing in that a fluid-bed coater with the name Innojet® AirCoater, from Innojet, Steinen, Germany was used in which a fluid bed was produced in which the steatite bodies circulated toroidally.

50 hollow cylinders were removed, cut in half and the layer thicknesses determined under the microscope at 4 points at 90° intervals. The layer thickness of a hollow cylinder corresponds to the mean value of the 4 measured values. 90% of all the shaped bodies measured had a layer thickness of 130 μm.

Comparison Example 2

Formaldehyde (FA) Catalyst

To produce a formaldehyde catalyst with an active-mass content (component a)) of 20 wt.-%, a solids content of an organic binding agent (component b)) of 20 wt.-% and a solids content of an inorganic adhesion-promoting component (component (c)) of 1 wt.-%, in a fluid-bed coater (Unilab®, Oystar Huttlin, Schopfheim, Germany), 700 g of steatite bodies (density 2.7 $g/cm^3$) in the form of hollow cylinders measuring 5×5×2.5 mm were coated with a suspension which was produced as follows:

1100 ml of demineralized water was placed in a glass container. 184 g of the active-mass powder (mixture of $Fe_2(MoO_4)_3$ and $MoO_3$, (produced according to example 1 of EP 1 674 156 A1 (molar ratio (Mo:Fe=2.5))) is suspended accompanied by stirring. For better homogenization, the suspension is treated for 3 min, setting 6, with an Ultra-Turrax®. Accompanied by stirring, 9.22 g of $ZrO_2$ sol (20% solids content, acetate-stabilized, from Nyacol, trade name: NYACOL® Zirconia (acetates)) is added. The pH of the suspension is set at 4 with a 25% ammonia solution. 92 g of the organic binding agent (50% dispersion of water and vinyl acetate/ethylene copolymer, EP 65, from Air Products) is added to the suspension and the suspension homogenized for one hour accompanied by stirring.

For the coating, the suspension was sprayed onto a fluid bed produced by means of process air temperature-controlled at 80° C.

50 hollow cylinders were removed, cut in half and the layer thicknesses determined under the microscope at 4 points at 90° intervals. The layer thickness of a hollow cylinder corresponds to the mean value of the 4 measured values. 74% of all the shaped bodies measured had a layer thickness of 300 μm.

Example 2

Catalysts were produced analogously to comparison example 2, differing in that a fluid-bed coater with the name Innojet® AirCoater, from Innojet, Steinen, Germany was used in which a fluid bed was produced in which the steatite bodies circulated toroidally.

50 hollow cylinders were removed, cut in half and the layer thicknesses determined under the microscope at 4 points at 90° intervals. The layer thickness of a hollow cylinder corresponds to the mean value of the 4 measured values. 88% of all the shaped bodies measured had a layer thickness of 250 µm.

Comparison example 3

Acrylic Acid Catalyst

To produce a catalyst with an active-mass content (component a)) of 20 wt.-%, a solids content of an organic binding agent (component b)) of 20 wt.-% and a solids content of an inorganic adhesion-promoting component (component (c)) of 1 wt.-%, in a fluid-bed coater (Unilab®, Oystar Huttlin, Schopfheim, Germany), 700 g of steatite bodies (density 2.7 g/cm$^3$) in the form of hollow cylinders measuring 5×5×2.5 mm were coated with a suspension which was produced as follows:

1100 ml of demineralized water is placed in a glass container. 184 g of an active-mass powder (Cu/MoVWO$_x$) is suspended accompanied by stirring. For better homogenization, the suspension is treated for 3 min, setting 6, with the Ultra-Turrax®. Accompanied by stirring, 9.22 g of a ZrO$_2$ sol (20% solids content, acetate-stabilized, from Nyacol, trade name: NYACOL® Zirconia (acetates)) is added to it. The pH of the suspension is set at 4 with a 25% ammonia solution. 92 g of an organic binding agent (50% dispersion of water and vinyl acetate/ethylene copolymer, EP 65, from Air Products) is added to the suspension and the suspension homogenized for one hour accompanied by stirring.

For the coating, the suspension was sprayed onto a fluid bed produced by means of process air temperature-controlled at 80° C.

50 hollow cylinders were removed, cut in half and the layer thicknesses determined under the microscope at 4 points at 90° intervals. The layer thickness of a hollow cylinder corresponds to the mean value of the 4 measured values. 72% of all the shaped bodies measured had a layer thickness of 2480 µm.

Example 3

Catalysts were produced analogously to comparison example 3, differing in that a fluid-bed coater with the name Innojet® AirCoater, from Innojet, Steinen, Germany was used in which a fluid bed was produced in which the steatite bodies circulated toroidally.

50 hollow cylinders were removed, cut in half and the layer thicknesses determined under the microscope at 4 points at 90° intervals. The layer thickness of a hollow cylinder corresponds to the mean value of the 4 measured values. 92% of all the shaped bodies measured had a layer thickness of 1680 µm.

DRAWINGS

Figure 1B:
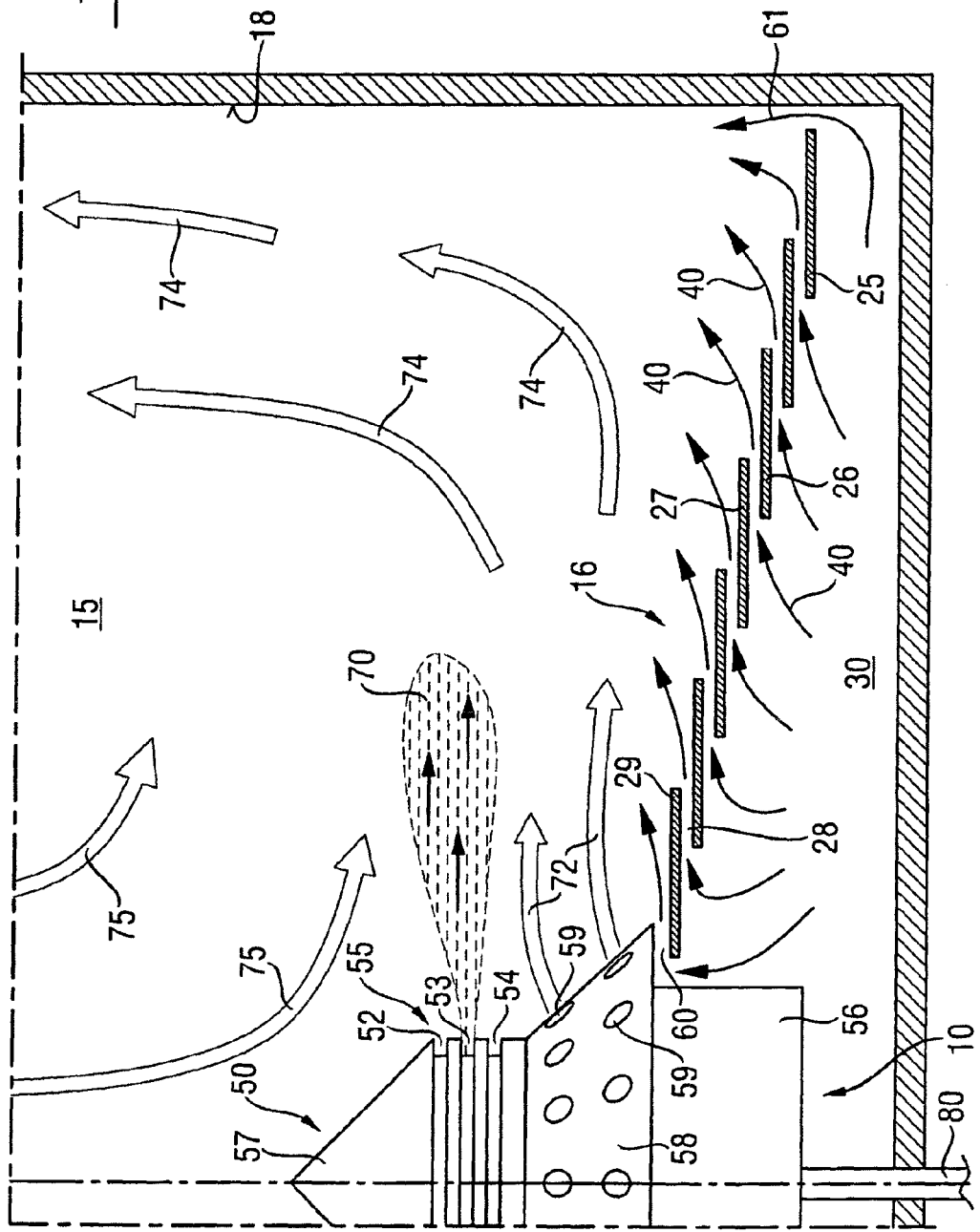
Figure 2A:
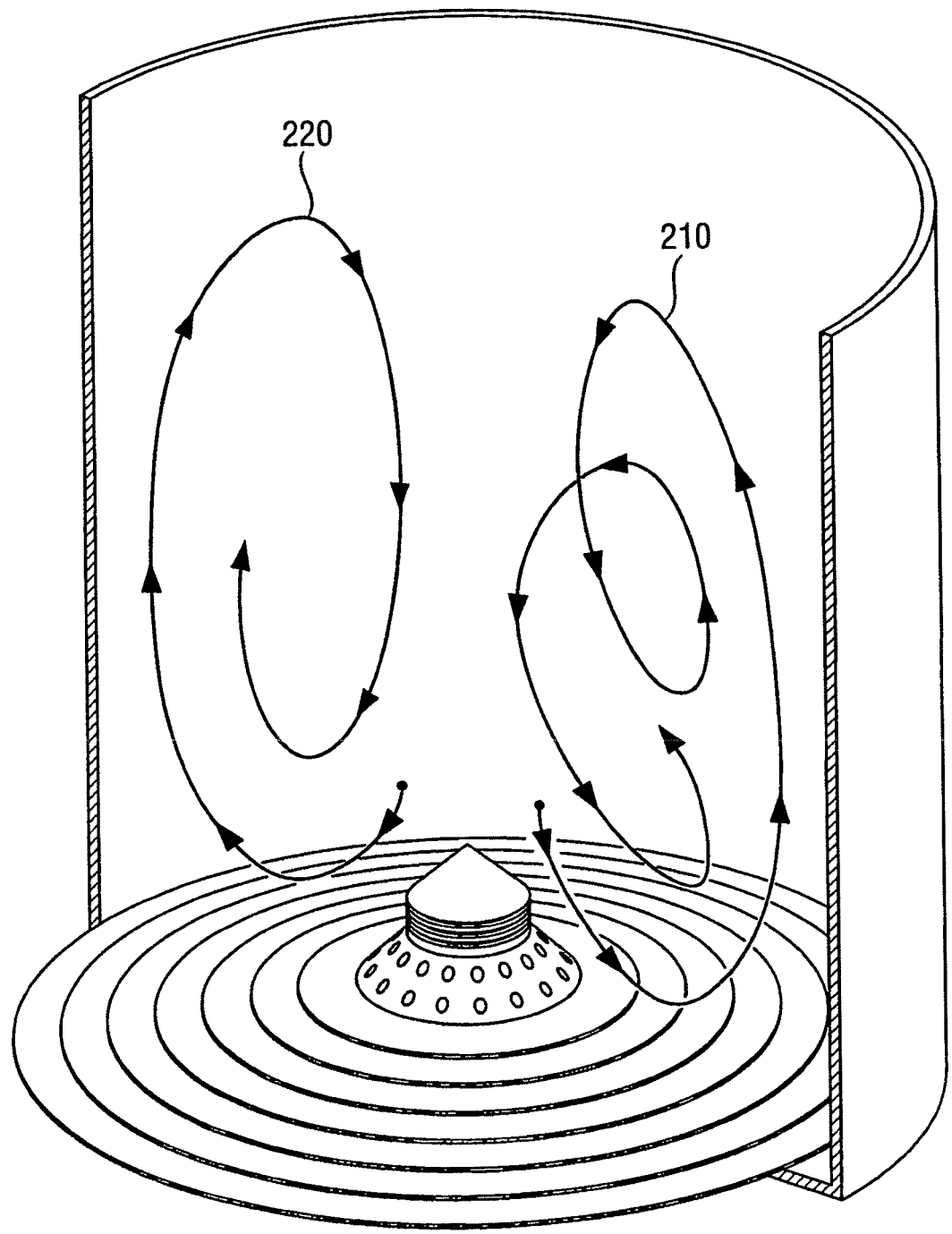
Figure 3A:
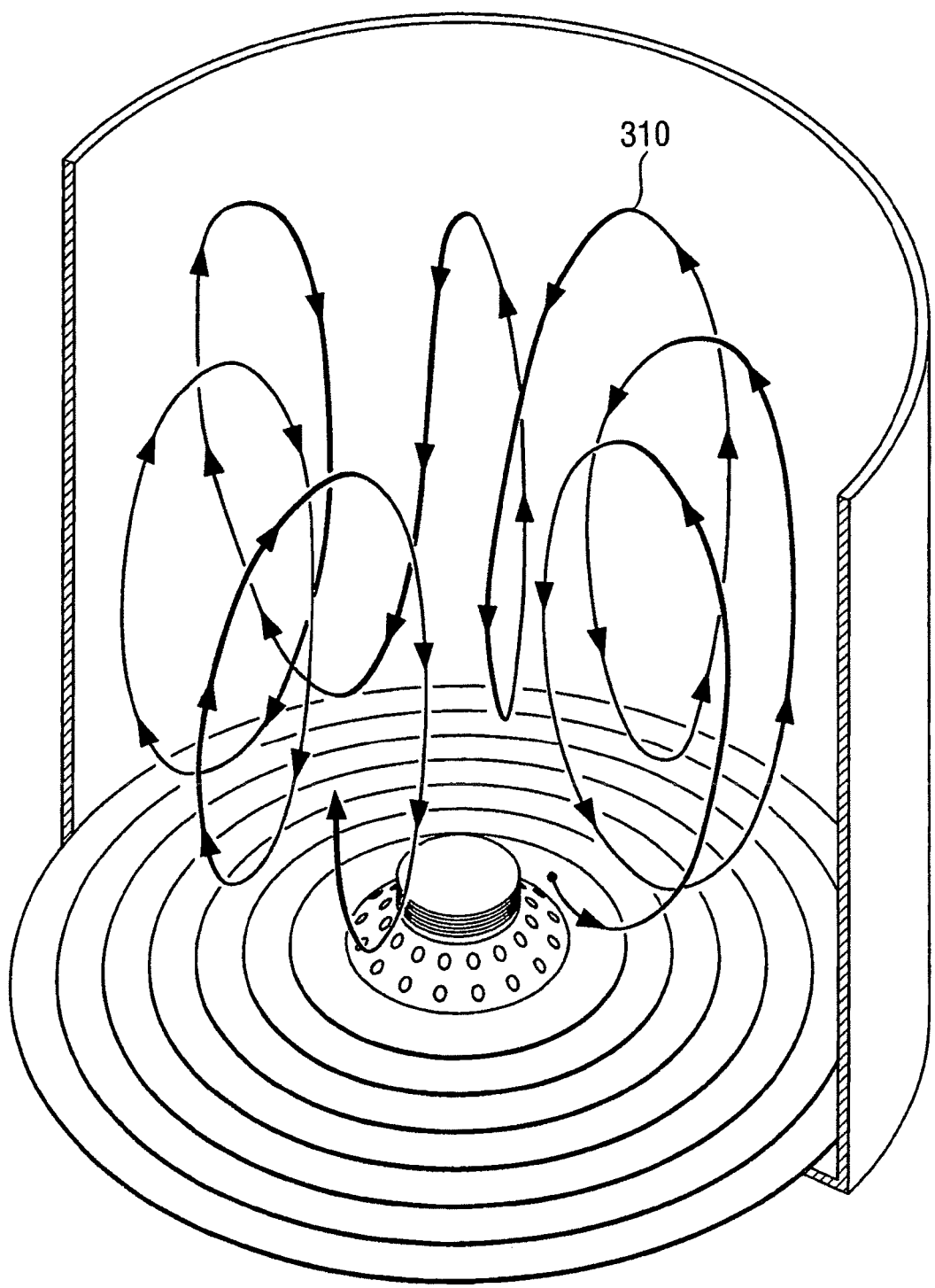
Figure 3B:
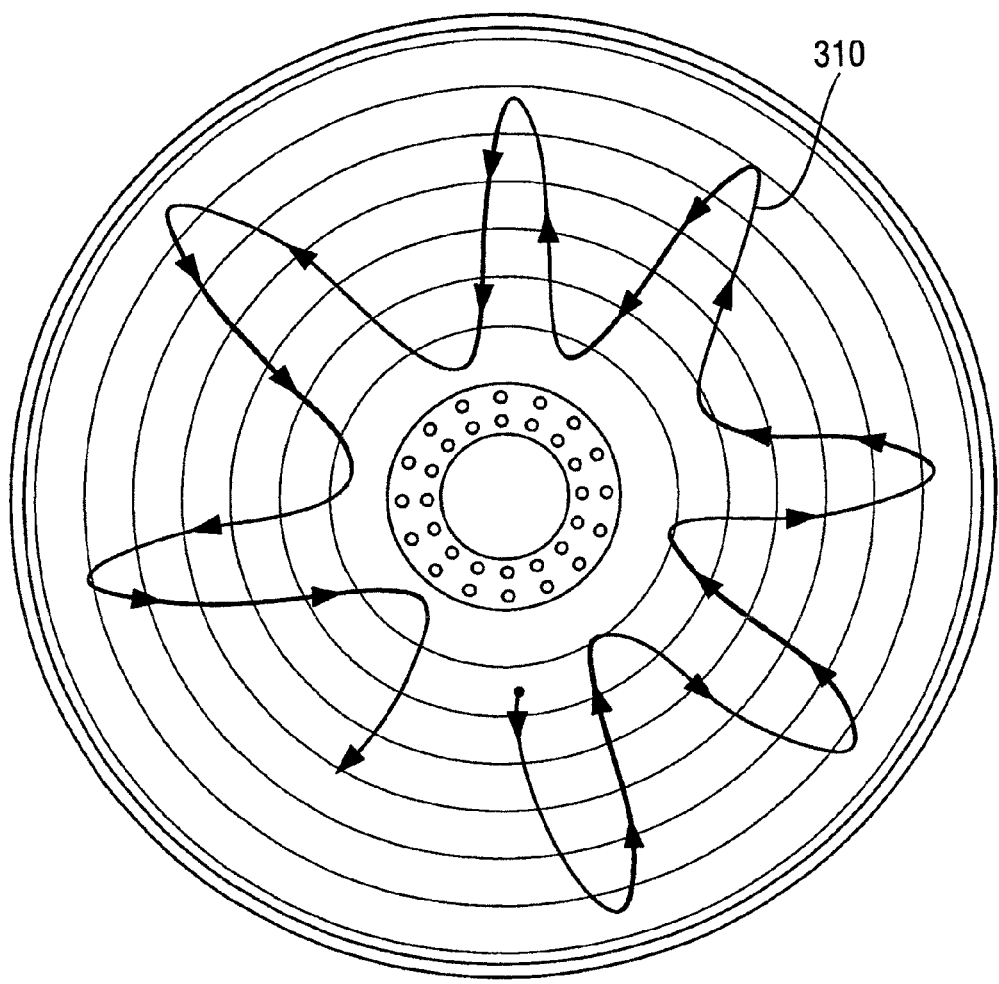

The following description of a preferred device for carrying out the method according to the invention and also the description of movement paths of catalyst support shaped bodies as support structures serve, in connection with the drawing, to explain the invention. There are shown in:

FIG. 1A a vertical sectional view of a preferred device for carrying out the method according to the invention;

FIG. 1B an enlargement of the framed area in FIG. 1A numbered 1B;

FIG. 2A a perspective sectional view of the preferred device, in which the movement paths of two elliptically circulating catalyst support shaped bodies are represented schematically;

FIG. 2B a plan view of the preferred device and the movement paths according to FIG. 2A;

FIG. 3A a perspective sectional view of the preferred device, in which the movement path of a toroidally circulating catalyst support shaped body is represented schematically;

FIG. 3B a plan view of the preferred device and the movement path according to FIG. 3A.

A device, numbered 10 as a whole, for carrying out the method according to the invention is shown in FIG. 1A.

The device 10 has a container 20 with an upright cylindrical side wall 18 which encircles a process chamber 15.

The process chamber 15 has a bottom 16 below which is a blowing chamber 30.

The bottom 16 consists of a total of seven annular plates, laid one over the other, as guide plates. The seven annular plates are positioned one over another in such a way that an outermost annular plate 25 forms an undermost annular plate on which the other six inner annular plates, each one partially overlapping the one beneath it, are then placed.

For the sake of clarity, only some of the total of seven annular plates have reference numbers, for example the two overlapping annular plates 26 and 27. Due to this overlapping and spacing, there is formed in each case between two annular plates an annular slot 28 through which process air 40 can pass as a process gas, with a predominantly horizontally aligned movement component, through the bottom 16.

An annular gap nozzle 50 is inserted from below in the central opening of the central uppermost inner annular plate 29. The annular gap nozzle 50 has a mouth 55 which has a total of three orifice gaps 52, 53 and 54. All three orifice gaps 52, 53 and 54 are oriented so as to spray approximately parallel to the bottom 16, thus approximately horizontally, covering an angle of 360°. Alternatively, the spraying nozzle can be designed in such a way that the spraying cone runs diagonally upwards. Spray air is expressed as spray gas via the upper gap and the lower gap 54, the suspension to be sprayed is expressed through the central gap 53.

The annular gap nozzle 50 has a rod-shaped body 56 which extends downwards and contains the corresponding channels and feed lines which are known per se and therefore not represented in the drawing. The annular gap nozzle 50 can be formed for example with a so-called rotating annular gap, in which walls of the channel through which the solution is sprayed out rotate relative to each other, in order to avoid blockages of the nozzle, thus making possible a uniform spraying out from the gap 53 over the circumferential angle of 360°.

The annular gap nozzle 50 has a conical head 57 above the orifice gap 52.

In the area below the orifice gap 54 is a truncated-cone-shaped wall 58 which has numerous apertures 59. As can be seen from FIG. 1B, the underside of the truncated-cone-shaped wall 58 rests on the innermost annular plate 29 in such a way that a slot 60, through which process air 40 can pass, is formed between the underside of the truncated-cone-shaped wall 58 and the annular plate 29 lying below and partially overlapping with it.

The outer ring 25 is at a distance from the wall 18, with the result that process air 40 can enter the process chamber 15, with a predominantly vertical component, in the direction of the arrow given the reference number 61 and thereby gives the process air 40 entering the process chamber 15 through the slot 28 a component aligned relatively sharply upwards.

The right-hand half of FIG. 1A shows what relationships form in the device 10 after entry.

A spray cloud 70 of the suspension, the horizontal mirror plane of which runs roughly parallel to the bottom plane, emerges from the orifice gap 53. Air passing through the apertures 59 in the truncated-cone-shaped wall 58, which can be for example process air 40, forms a supporting air flow 72 on the underside of the spray cloud 70. A radial flow in the direction of the wall 18 by which the process air 40 is deflected upwards, as represented by the arrow given the reference number 74, is formed by the process air 40 passing through the numerous slots 28. The shaped bodies are guided upwards by the deflected process air 40 in the area of the wall 18. The process air 40 and the catalyst support shaped bodies to be treated then separate from each other, wherein the process air 40 is discharged through outlets, while the shaped bodies move radially inwards as shown by the arrow 75 and travel vertically downwards as a result of gravity in the direction of the conical head 57 of the annular gap nozzle 50. The shaped bodies moving downwards are deflected there, carried to the upperside of the spray cloud 70 and treated there with the sprayed medium. The sprayed shaped bodies then move again towards the wall 18 and away from each other in the process, as a much larger space is available to the shaped bodies at the annular orifice gap 53 after leaving the spray cloud 70. In the area of the spray cloud 70, the shaped bodies to be treated encounter the sprayed suspension and are moved in the direction of movement towards the wall 18, remaining apart from each other, and treated, i.e. dried, very uniformly and harmonically with the heated process air 40.

Two possible movement paths of two elliptically circulating catalyst support shaped bodies are shown in FIG. 2A by means of the curve shapes given the reference numbers 210 and 220. The elliptical movement path 210 displays relatively large variations in the size of the major and minor axes compared with an ideal elliptical path. The elliptical movement path 220, on the other hand, displays relatively little variation in the size of the major and minor axes and describes close to an ideal elliptical path without a circumferential (horizontal) movement component, as can be seen from FIG. 2B.

A possible movement path of a toroidally circulating catalyst support shaped body is shown in FIG. 3A by means of the curve shape given the reference number 310. The toroidally running movement path 310 describes a section of the surface from a virtually uniform torus, the vertical cross-section of which is elliptical and the horizontal cross-section of which is annular. FIG. 3B shows the movement path 310 in plan view.

The invention claimed is:

1. A method for applying a washcoat suspension to a support structure, wherein the method is carried out using a device (10) which is set up to produce, by means of a process gas (40) a fluid bed of support structures in which the support structures circulate elliptically or toroidally said method comprising the steps of:
   a) charging the device (10) with support structures and producing a support-structure fluid bed by means of a process gas (40), wherein the support structures circulate in the fluid bed elliptically or toroidally;
   b) impregnating the support structures with a washcoat suspension by spraying the support structures circulating elliptically or toroidally in the fluid bed with the washcoat suspension;
   c) drying the support structures sprayed with the washcoat suspension; and
   d) optionally calcining the support structures loaded with the solids contents of the washcoat suspension.

2. The method according to claim 1, wherein the device (10) comprises a process chamber (15) with a bottom (16) in the centre of which bottom an annular gap nozzle (50) is arranged.

3. The method according to claim 2, wherein the process chamber (15) furthermore comprises a side wall (18), wherein the process gas (40) is fed, with a horizontal movement component aligned radially outwards, into the process chamber (15) through the bottom (16) of the process chamber (15), the bottom being constructed of several overlapping annular guide plates laid one over the other (25, 26, 27, 29) between which annular slots (28) are formed, in order to produce the support-structure fluid bed.

4. The method according to claim 3, wherein the process gas (40) fed into the process chamber (15) is subjected to a circumferential flow component.

5. The method according to claim 4, wherein the process gas (40) fed into the process chamber (15) is subjected to the circumferential flow component by means of guide elements which are arranged between the annular guide plates (25, 26, 27, 29).

6. The method according to claim 4, wherein the process gas (40) fed into the process chamber (15) is subjected to the circumferential flow component by feeding an additional process gas (61), with a movement component aligned diagonally upwards, through the bottom (16) of the process chamber (15) into the process chamber (15) in the area of the side wall (18) of the process chamber (15).

7. The method according to claim 2, wherein the annular gap nozzle (50) atomizes a spray cloud (70) of the washcoat suspension which runs parallel to the plane of the bottom (16).

8. The method according to claim 7, wherein the mouth (55) of the annular gap nozzle (50) is embedded into the fluid bed.

9. The method according to claim 7, wherein a gas support cushion (72) is produced on the underside of the spray cloud (70).

10. The method according to claim 1, wherein the support structure is formed from a non-porous material or material mixture comprising steatite, quartz ($SiO_2$), porcelain, magnesium oxide, tin dioxide, silicon carbide, rutile, alumina ($Al_2O_3$), aluminium silicate, magnesium silicate, zirconium silicate, cerium silicate or mixtures of two or more of the above materials.

11. The method according to claim 1, wherein the support structure has a hardness greater than/equal to 20 N.

12. The method according to claim 1, wherein the process gas (40) is selected from the group consisting of air, oxygen, nitrogen and the noble gases.

13. The method according to claim 1, wherein the process gas (40) is heated, preferably to a temperature of more than/equal to 40° C.

14. The method according to claim 1, wherein the process gas (40) is enriched, before being fed into the process chamber (15), with the suspending agent of the washcoat suspension in a range of 10 to 50% of the saturation vapour pressure.

15. The method according to claim 1, wherein the support structure is formed as a sphere, cylinder, perforated cylinder, trilobe, tetralobe, ring, doughnut, star, cartwheel or strand.

16. The method according to claim 1, wherein the washcoat suspension contains $TiO_2$, $V_2O_5$ and $Sb_2O_3$ in particulate form.

17. The method according to claim 16, wherein the suspension furthermore comprises a phosphate compound, an alkali and/or alkaline earth compound, and an organic and/or inorganic binding agent.

18. The method according to claim 16, wherein the washcoat suspension is sprayed onto a ring as support structure.

19. The method according to claim 1, wherein the washcoat suspension contains iron molybdate.

20. The method according to claim 1, wherein the washcoat suspension contains a mixed oxide of Mo, V and W, or Mo, V and Nb, or Ta as well as optionally Te or Sb, which is optionally doped with Cu, Mn or Fe.

21. The method of claim 1, wherein a device (10) produces, by means of a process gas (40), a fluid bed of support structures in which the support structures circulate elliptically or toroidally for applying a washcoat suspension to a support structure.

22. The method of claim 21, wherein the device (10) comprises a process chamber (15) with a bottom (16) in the centre of which bottom an annular gap nozzle (50) is arranged.

23. The method of claim 22, wherein the process chamber (15) furthermore comprises a side wall (18), wherein the bottom (16) is constructed of several overlapping annular guide plates laid one over another (25, 26, 27, 29) between which annular slots (28) are formed via which process gas (40) can be fed in with a horizontal movement component aligned radially outwards.

24. The method of claim 23, wherein guide elements which impose a circumferential flow component on the process gas passing through are arranged between the annular guide plates (25, 26, 27, 29).

25. The method of claim 22, wherein the mouth (55) of the annular gap nozzle (50) is formed such that with the nozzle (50) a spray cloud (70) can be sprayed which runs parallel to the bottom plane.

26. The method of claim 25, wherein outlets (59) for support gas are provided between the mouth (55) of the annular gap nozzle (50) and the bottom (16) lying beneath it, in order to produce a support cushion on the underside of the spray cloud (70).

27. The method of claim 26, wherein the support gas can be provided by the annular gap nozzle (50) itself and/or by the process gas (40).

28. The method of claim 22, wherein the annular gap nozzle (50) has a conical head (57), and in that the mouth (55) runs along a circular circumferential line of a conical section.

29. The method of claim 22, wherein there is arranged in the area between the mouth (55) of the nozzle (50) and the bottom (16) lying beneath it a truncated-cone-shaped or hyperbolic wall (58) which preferably has passage openings (59) for support gas.

30. The method of claim 29, wherein an annular slot (60) for the passage of process gas (40) is formed between the underside of the truncated-cone-shaped or hyperbolic wall (58) and the bottom (16) lying beneath it.

31. The method of claim 22, wherein the position of the mouth (55) of the nozzle (50) is height-adjustable.

32. A shell catalyst produced according to the method of claim 1, comprising a shaped body to which a shell comprising a metal-oxide material is applied, wherein the shell catalyst is an element of a batch of a plurality of shell catalysts, wherein the ratio of the standard deviation of the shell thicknesses of the shell catalysts of the batch to the mean value of the shell thicknesses of the shell catalysts of the batch is smaller than/equal to 20%.

* * * * *

UNITED STATES PATENT AND TRADEMARK OFFICE
CERTIFICATE OF CORRECTION

PATENT NO.        : 8,722,565 B2                                              Page 1 of 1
APPLICATION NO.   : 12/601876
DATED             : May 13, 2014
INVENTOR(S)       : Mestl et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 608 days.

Signed and Sealed this

Twenty-ninth Day of September, 2015

Michelle K. Lee
*Director of the United States Patent and Trademark Office*